(12) United States Patent
Kinast (10) Patent No.: US 6,377,845 B1
(45) Date of Patent: Apr. 23, 2002

(54) METHOD AND DEVICE FOR SENSING IMPEDANCE RESPIRATION

(75) Inventor: Eric Kinast, Santa Ana, CA (US)

(73) Assignee: Datascope Investment Corp., Montvale, NJ (US)

( * ) Notice: Subject to any disclaimer, the term of this patent is extended or adjusted under 35 U.S.C. 154(b) by 108 days.

(21) Appl. No.: 09/625,013

(22) Filed: Jul. 25, 2000

(51) Int. Cl.[7] .................................................. A61B 5/05
(52) U.S. Cl. ....................................................... 600/547
(58) Field of Search ................................. 600/547, 535

(56) References Cited

U.S. PATENT DOCUMENTS

| | | | |
|---|---|---|---|
| 4,300,574 A | * | 11/1981 | Briggs .......................... 600/547 |
| 4,578,635 A | * | 3/1986 | Mee et al. ................... 600/547 |
| 5,025,784 A | * | 6/1991 | Shao et al. .................. 600/547 |
| 6,011,992 A | * | 1/2000 | Hubbard et al. ............ 600/547 |

* cited by examiner

*Primary Examiner*—Max Hindenburg
(74) *Attorney, Agent, or Firm*—Abraham Ronai

(57) ABSTRACT

An improved method and device for measuring transthoracic impedance through an ECG cable and electrodes, in which the measurement accuracy is substantially unaffected by shunt capacitance and series resistance within the cable, said device comprising a means for repetitively injecting alternating polarity impulses of charge into the ECG cable and electrodes, a demodulator, and a low pass filter. The measurement performed by integration of the transient voltage induced by the injected charge responds primarily to the resistive components of the cable and patient impedance, and substantially rejects the effects of the shunt capacitance.

41 Claims, 4 Drawing Sheets

METHOD AND DEVICE FOR SENSING IMPEDANCE RESPIRATION

BACKGROUND OF THE INVENTION

1. Field of the Invention

The invention relates to devices that measure the electrical impedance of body tissues, and in particular an impedance pneumograph utilizing a cable and electrodes also used for ECG monitoring.

2. Description of the Prior Art

The electrical impedance of the thorax varies cyclically with each breath. This property has been exploited to monitor the respiration activity of a person, by monitoring the thoracic impedance. By detecting these variations in the thoracic impedance an instrument is able to monitor respiratory activity. The impedance of the thorax may be measured by means of electrodes placed on the chest. Single-function instruments that measure respiratory activity by means of impedance find wide commercial use, particularly in the areas of sleep apnea monitoring. However, respiration monitoring capability is frequently included as part of more complex monitoring devices which serve other functions as well. Since the monitoring of the electrocardiogram (ECG) also requires placement of electrodes on the chest, in positions useful for respiration monitoring, it has become common practice to integrate a respiration monitoring feature into ECG monitoring devices.

In cases where respiration monitoring and ECG are combined, the respiration monitor shares the cable, leadwires, and electrodes with the ECG function. The respiration and ECG monitoring subsystems must be designed such that they do not produce mutual interference. This places constraints on the design of the respiration circuit, and how it may be coupled to the patient through the ECG cable and electrodes. Many instruments accept ECG cables conforming to legacy designs, which predate widespread use of respiration monitoring. As such, the design of these cables is not optimized for respiration monitoring. This forces certain compromises in the design of the respiration monitoring subsystem. Further, there are several different cable constructions in common use, having varying impacts on the design and performance of the respiration circuit.

Due to the above practical limitations of the known art, most equipment manufacturers restrict the application of their respiration monitor to a particular class of cables for which their design has been optimized. In cases where a manufacturer wishes to accept widely differing cables, such as to accept the cables used by a different manufacturer, it may be necessary to modify or recalibrate the respiration circuit for optimal performance. Even when this is not the case, the present art restricts the user to a limited set of cables and accessories, which were contemplated when the respiration circuit was designed and calibrated. Greater flexibility in the application of a respiration monitoring subsystem would be possible if the device were capable of accepting a broad range of cable parameters and patient conditions without the need for modification or recalibration.

SUMMARY OF THE INVENTION

Accordingly, it is an object of the invention to produce an impedance respiration monitoring circuit, the sensitivity of which does not vary appreciably over a wide range of cable shunt capacitance and series resistance, and patient baseline resistance.

It is another object of the invention to produce an impedance respiration monitoring circuit, which can be coupled to existing ECG electrodes with minimal degradation of ECG performance.

To achieve the foregoing and other objects, the invention, in accordance with certain of its aspects, provides an improved method for measuring the resistive component of the combined total impedance of the patient, electrodes, and cable, said method comprising the steps of:

(a) injecting as an impulse a known quantity of charge into the total impedance to be measured, causing a voltage to be developed across said impedance; and (b) integrating said voltage, the period of integration being substantially longer than the exponential decay time constants of said impedance.

In accordance with other of its aspects, the invention provides apparatus for practicing the foregoing method, which comprises:

(a) a voltage generator delivering a substantially rectangular pulse or square wave, having a half-period significantly longer than the exponential decay time constants of the impedance to be measured;

(b) an essentially capacitive coupling network differentiating said pulse or square wave, and injecting charge to the impedance to be measured;

(c) a receiving circuit, consisting of either an asynchronous rectifier or synchronous demodulator, which detects the voltage developed across the impedance to be measured following the injection of the charge; and (d) a low pass filter having a time constant much longer than the period of generator (a).

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

DETAILED DESCRIPTION OF THE PREFERRED EMBODIMENTS

Respiratory activity causes motion of the thorax, accompanied by deformation of the tissues. Deformation of an electrical conductor causes a change in the electrical resistance of the conductor. Therefore, it is possible to observe respiratory activity by monitoring the electrical resistance of the thorax, and observing the modulation of this impedance with each breath. This measurement can be performed by electrodes attached to the skin in the thoracic region, and connected to suitable instrumentation. Suitable electrodes are often already in place as a consequence of ECG monitoring. Therefore, it is preferable to use the existing ECG electrodes, as well as the associated ECG cables and leadwires, for respiration monitoring.

The sharing of electrodes between ECG and respiration monitoring places design constraints on the respiration instrumentation. The measurement of thoracic resistance may not use a DC current, as this may interfere with the ECG acquisition, and may cause polarization of the electrodes. It is therefore common practice to measure the thoracic impedance using an AC current, having a frequency well outside the ECG bandwidth. However, the use of a high-frequency respiration measuring current causes problems due to the capacitance of the ECG cables and leadwires. This capacitance can cause errors in measurement, as it appears in shunt with the thoracic impedance. Driven shields and similar techniques are sometimes used in electronic instrumentation, such as impedance bridges, to minimize the effects of cable capacitance. However, the design of commonly used ECG cables does not admit to the use of these techniques. Therefore, other means of compensating for the effects of cable capacitance must be used.

Further, it is necessary to couple the respiration instrumentation to the ECG terminals in a manner that does not cause degradation of the ECG performance. ECG amplifiers have a fairly high input impedance, and must function in the presence of large common-mode interference signals, such as power line frequency pick-up. Therefore, the coupling of the respiration circuits must provide a very high impedance at ECG band frequencies, and must not degrade the common mode rejection of the ECG amplifier by producing significantly unbalanced loading.

At the electrodes, the respiration signal consists of a small respiratory impedance modulation, on the order of one ohm, and often less, superimposed on a larger baseline impedance, ranging from a few hundred to a few thousand ohms. A respiration monitor generally discards the baseline component of the impedance measurement, the small respiratory modulation being the component of interest. The patient impedance is seen through a connecting cable, which adds various series and shunt impedances. ECG cables generally consist of two portions, a trunk cable and the electrode leadwires. The trunk portion of the cable spans from the monitoring instrument to the immediate proximity of the patient. At this point, in a fixture often referred to as the yoke, the trunk cable splits into the individual leadwires, which in turn connect to the individual electrodes. The leadwires are often detachable from the yoke. Many ECG cables contain integral series resistors, intended to provide protection during defibrillator discharge. In standard commercial practice, these resistors consist of nominally 1000 ohms placed in series with each active wire of the cable. They may be located either within the cable's instrument connector, or within the yoke. Shunt impedance exists in the form of the cable's wire-to-wire and wire-to-shield capacitance. The leadwires may add additional shunt capacitance, particularly when shielded.

Although an ECG cable may contain several active wires, connected to several electrodes, respiration monitoring is generally performed across a selected pair of the electrodes. According to the construction of the cable, the wires may be unshielded, may have only an overall outer shield, or may have individual shields. In the latter case, it is customary to connect all of the individual shields to a single point, generally referenced to the ECG circuit common. The respiration circuit is generally either floating with respect to the ECG common, or is a balanced differential circuit with respect to the ECG common. In either case, the voltage induced by the respiration circuit is expressed symmetrically on the pair of wires connected to the selected electrodes. The symmetry noted above allows the equivalent circuit of the cable to be simplified, facilitating analysis of the interactions between various forms of respiration circuits and the cable parameters.

Figure 3:
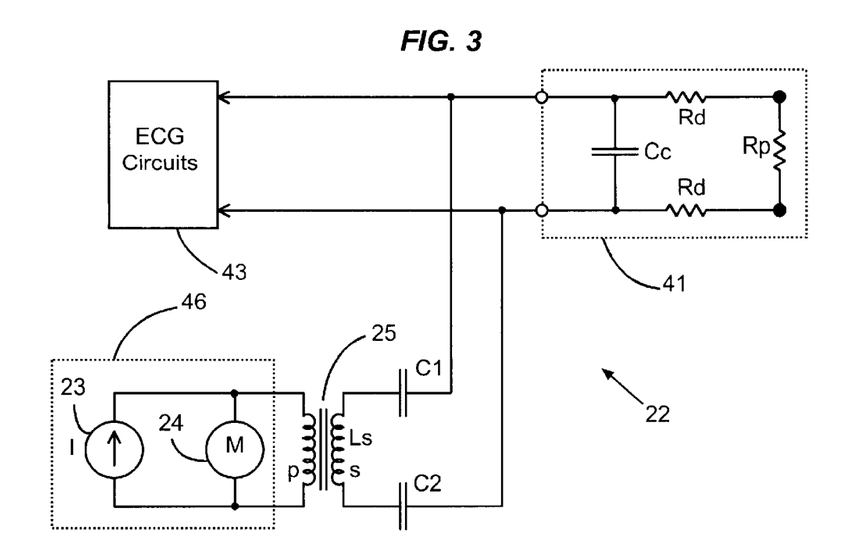
FIG. 3 is a model circuit of the known art, incorporating means of coupling to ECG circuits using an isolating transformer and capacitors.
Figure 4:
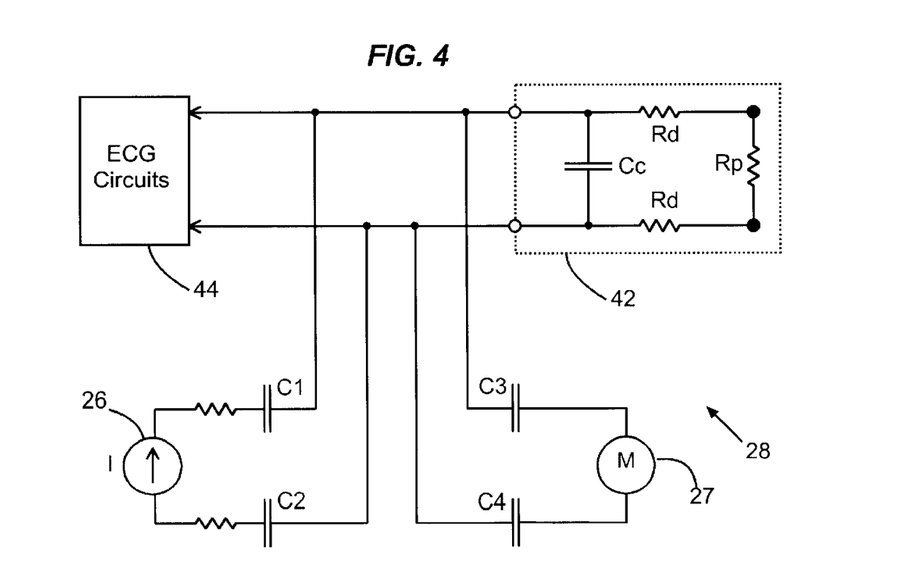
FIG. 4 is a model circuit of an alternate known art, incorporating coupling by small-value capacitors.
Figure 5:
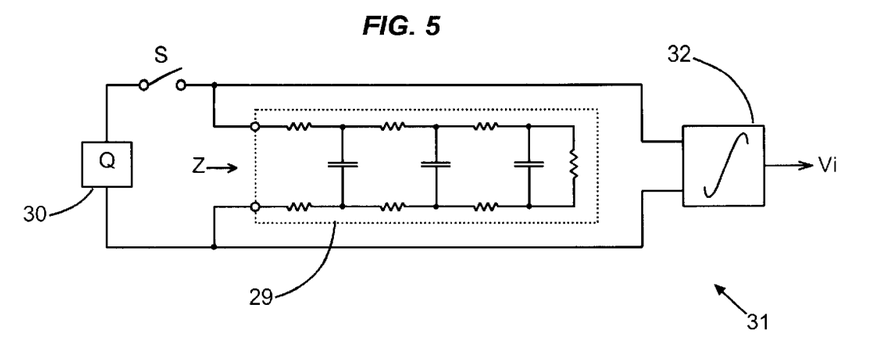
FIG. 5 is a model circuit of the present invention, incorporating a charge reservoir and an integrator, demonstrating the principal of measurement of resistance by charge injection and integration.
Figure 6:
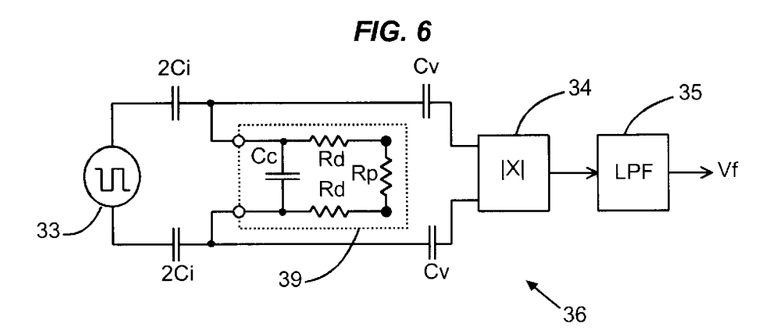
FIG. 6 is a model circuit of a the preferred embodiment of the present invention, based on the measurement principal of charge injection and integration.

FIGS. 1A–4, and related background discussion below, will reveal the advantages of the present invention, illustrated in FIGS. 5–6. Specifically, in FIGS. 1A–1C a simplified model of an ECG cable is presented allowing for analysis between various forms of respiration circuits and cable parameters. Use of this simplified model is made to examine a prior art simple respiration impedance measuring circuit and also to examine a prior art model circuit incorporating a means for coupling to ECG circuits. Analysis of said model circuits will reveal the disadvantages of the prior art and how the present invention, as illustrated in FIGS. 5–6, overcomes these disadvantages.

Figure 1A:
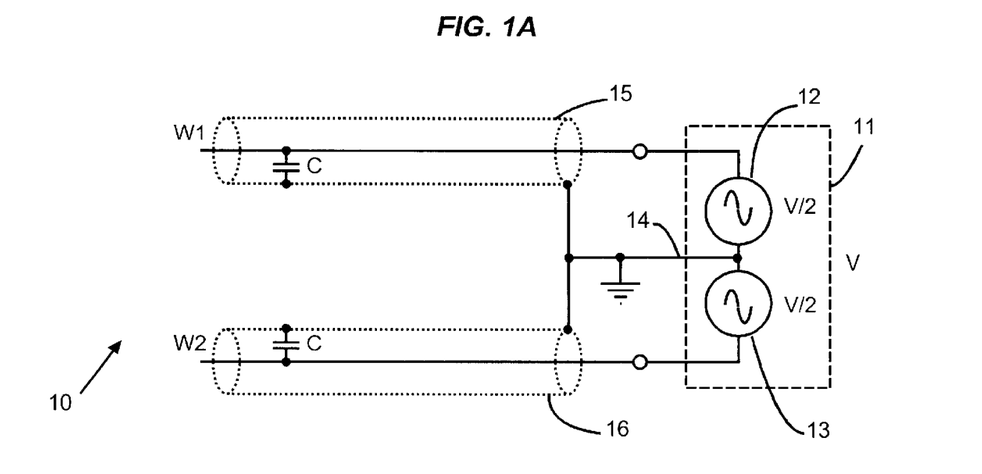
FIG. 1A is a model circuit of a shielded cable connected to a generator representing a respiration circuit, illustrating the cable capacitance.
Figure 1B:
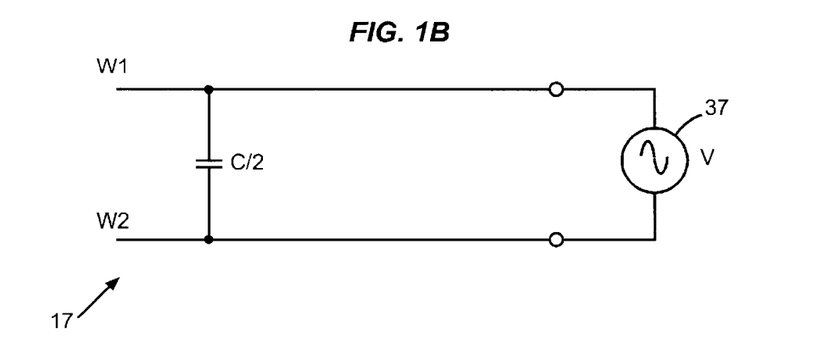
FIG. 1B is a simplified version of the model circuit of FIG. 1A.
Figure 1C:
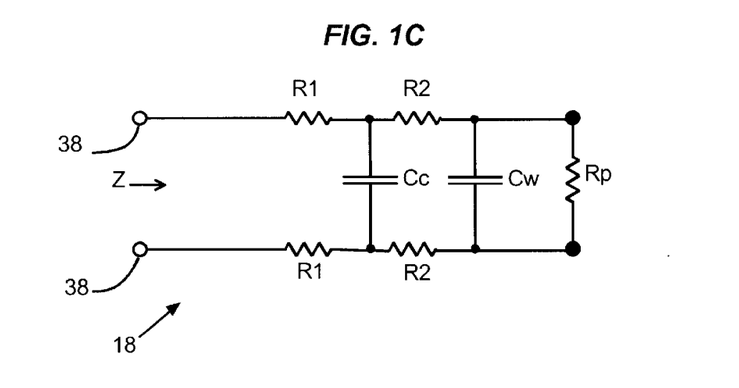
FIG. 1C is a circuit network modeling the capacitive and resistive elements of a patient resistance connected to an ECG cable.

In FIG. 1A, FIG. 1B, and FIG. 1C, the development of a simplified model of an ECG cable is presented. As illustrated in FIG. 1A, circuit 10 comprises two identical shielded wires, W1 and W2, surrounded by shields 15 and 16 (shown in dotted lines), and center-tapped voltage generator 11, also circumscribed by a dotted line. The wires W1 and W2 represent a portion of an ECG cable, each possessing a capacitance, labeled C, between the wire and the associated shield. Voltage generator 11 delivers a total voltage, labeled V, across wires W1 and W2. Voltage V represents the voltage that would be induced across these wires by a respiration circuit. Since this voltage is, as described above, considered to be applied symmetrically, voltage generator 11 is internally modeled as two equal series-connected voltage generators 12 and 13, each delivering equal voltages labeled V/2. The midpoint of generators 12 and 13, comprising the circuit branch designated 14, is connected to shields 15 and 16, and represents the common point of circuit 10. Since circuit 10 is completely symmetrical, by inspection no current flows in circuit branch 14. Network theory states that branches of a circuit carrying zero current may be removed without affecting the circuit. Accordingly, if branch 14 is removed, the two capacitances labeled C become in effect series connected across the total voltage of generator 11. The two series connected capacitances can be replaced by their equivalent, a single capacitance of value one-half C. This rearrangement is shown by circuit 17 in FIG. 1B. Circuit 17 comprises a single capacitance of one-half C, labeled C/2, connected across wires W1 and W2, driven by generator 37. Generator 37 is equivalent to generator 11, with the center tap no longer shown. Because of symmetry, the more complex circuit 10 of FIG. 1A can be represented by the simplified model circuit 17 of FIG. 1B. Although the individual capacitances C in original circuit 10 did not clearly appear to be in shunt with the respiration circuit modeled by generator 11, the foregoing analysis shows that this is indeed the case, as is illustrated by the equivalent model circuit 17. Therefore, even in the case of individually shielded wires, an equivalent wire-to-wire shunt capacitance is presented to the respiration circuit. Other cable constructions, such as a cable with only an outer shield, possess actual wire-to-wire capacitance, in addition to the equivalent capacitance due to the shield. These may be combined into a single effective wire-to-wire capacitance for analysis of the respiration circuits.

The above analysis indicates that ECG cables and leadwires can be modeled in terms of equivalent shunt capacitances, without concern for the particular configuration of the shielding of the cable and leadwires. This method of modeling has been used in FIG. 1C to develop a generalized equivalent circuit 18 that may be used to represent the various cable constructions described above. The resistance labeled Rp represents the patient impedance at the electrodes. The terminals designated 38 represent the point at which the ECG and respiration monitoring instrument would be connected to the cable. The capacitance labeled Cc represents the equivalent shunt capacitance presented by the trunk portion of the ECG cable. The capacitance labeled Cw represents the equivalent shunt capacitance presented by the leadwires. Defibrillation protection resistors may be located either at the instrument connector, or at the yoke where the leadwires join to the cable trunk. The pair of resistors labeled R1 model defibrillation protection resistors located at the instrument connector, while the pair of resistors labeled R2 represent protection resistors located at the yoke. Impedance Z, seen looking into the terminals 38, is the patient impedance as seen by a respiration impedance measuring circuit (not shown), including the effects of the cable and leadwires. Circuit 18 is therefore a generalized model network that can be used to analyze the operation of various types of respiration monitoring circuits connected to the terminals 38.

Figure 2A:
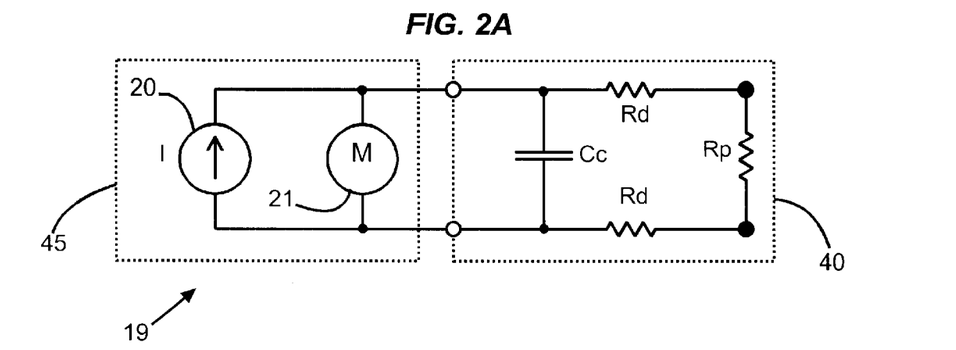
FIG. 2A is a model circuit of the basic form of the known art.

Turning attention to FIG. 2A, a specific instance of the general model network developed above is used to analyze a simple respiration impedance measuring circuit, representing a fundamental principal of the known art. FIG. 2A illustrates a simple respiration circuit 19 comprising network 40 and measuring circuit 45, each circumscribed by a dotted line. Network 40 represents a particular instance of the generalized network 18 of FIG. 1C, in which the cable construction has the defibrillation protection resistors, labeled Rd, located within the yoke, and in which the leadwires are assumed to be unshielded and to have negligible capacitance. Measuring circuit 45 is an impedance measurement circuit and comprises current source 20, which delivers AC current, I, and voltage measurement device 21, which measures the AC voltage developed across network 40. In practice, voltage measurement device 21 may be some form of demodulator, but for the following discussion, it may assumed to be simply an AC voltmeter, identified by the symbol M. The reading of M is proportional to the magnitude of the impedance presented by network 40, representing the cable and the patient. In a typical respiration monitor, current I might be a sinusoidal current at 50 kHz, and this current will be assumed in the following discussion.

Figure 2B:
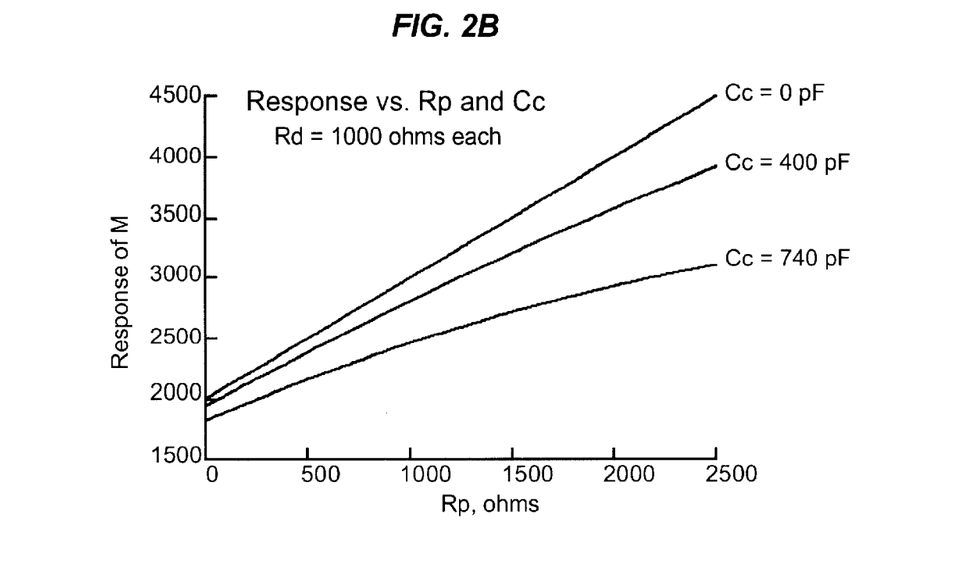
FIG. 2B is a graph showing the response of the circuit of FIG. 2A as a function of cable capacitance and patient resistance.
Figure 2C:
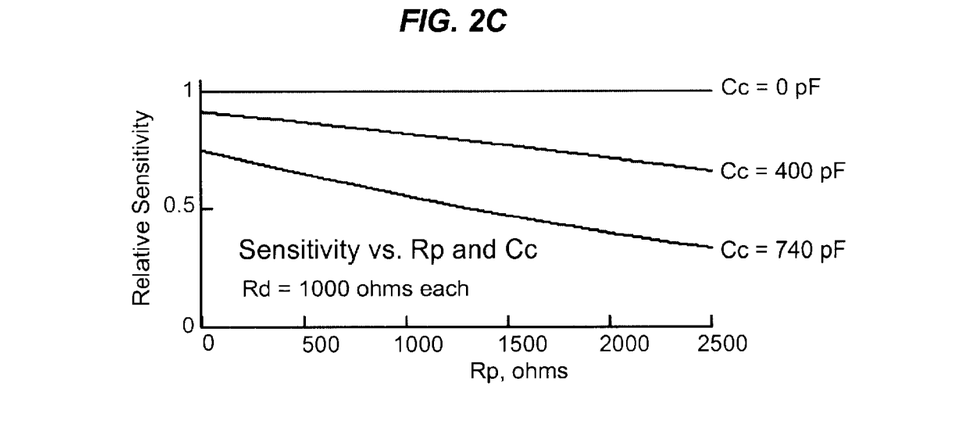
FIG. 2C is a graph showing the sensitivity of the circuit of FIG. 2A as a function of cable capacitance and patient resistance.

In FIG. 2B graphs are presented, showing the response of M vs. the patient resistance, labeled Rp, for various values of the cable capacitance, labeled Cc. For the ideal case where Cc is zero, M responds linearly to Rp as is desired. The curve for Cc=0 does not pass through the origin, but intercepts the Y axis at 2000 ohms, corresponding to the value of the two series defibrillation protection resistors labeled Rd. This is of no consequence, as the respiration monitor discards the baseline resistance, as has been discussed. The respiration signal is the small respiratory modulation of Rp, not the value of Rp itself. The sensitivity of the respiration circuit to this modulation is the local slope of the curves of FIG. 2B at the nominal value of Rp. FIG. 2C shows a plot of this sensitivity vs. Rp for various values of Cc. For the case where Cc=0, the sensitivity is constant for all values of Rp, as is desired.

The above is no longer true for real cables where Cc is greater than zero. In FIG. 2B the plots for Cc=400 pF and Cc=740 pF show pronounced curvature, due to the shunting effect of the capacitance Cc. This is more clearly demonstrated in FIG. 2C where the sensitivity can be seen to vary more than 3:1 over the range of Cc and Rp plotted. An instrument employing this respiration circuit would then experience a large change in sensitivity if use were attempted with a variety of cable capacitances and patient baseline resistances. Therefore, the respiration circuit design must be improved to reduce this variation, or the range of operating conditions must be restricted to a region where the sensitivity variation is tolerable.

One simple way to reduce the effects of the capacitance is to lower the operating frequency, since this increases the reactance of the shunt capacitance. However, the operating frequency should remain well outside the ECG bandpass, lest interference to the ECG circuits result. Further, as will be seen shortly, low operating frequencies complicate the already difficult problem of coupling the respiration circuits to the ECG cable and electrodes.

The simple circuit 19 of FIG. 2A shows only the means of respiration monitoring, and does not illustrate how the respiration and ECG circuits might be interconnected, allowing the same cable and electrodes to be shared for both purposes. A coupling means that minimizes mutual interference must be utilized. Circuit 22 in FIG. 3 illustrates one known art. Transformer 25, having a primary labeled p and a secondary labeled s, with secondary inductance labeled Ls, provides common-mode isolation between respiration circuit 46 and ECG circuits 43. Transformer primary, p, is connected to respiration impedance measurement circuit 46, containing AC current source 23 and voltage measuring instrument 24. Transformer secondary, s, is coupled to network 41, representing a patient and ECG cable. ECG circuit 43 is directly connected to network 41. Since the transformer secondary, s, has a low impedance in the ECG band of frequencies, due to its finite inductance Ls, it would effectively short-circuit the differential-mode ECG signals if connected directly to the ECG cable (modeled by network 41). Therefore, it is necessary to employ coupling capacitors, labeled C1 and C2, which are chosen to have a low impedance at the respiration measurement frequency, and a high impedance at the much lower ECG frequencies. Unfortunately, the selection of the capacitor value is at best a compromise. A capacitor large enough to provide a low impedance at the respiration measurement frequency is also large enough to cause some degradation of the ECG input impedance at certain important ECG band frequencies, such as at the 50 or 60 Hz power mains frequency. This provides an incentive to use a higher respiration measurement frequency, since this allows smaller coupling capacitors to be used. But to do so increases the troubles caused by the cable shunt capacitance, since the capacitive shunt impedance decreases with increasing frequency.

Some commercial instruments attempt to reduce the effects of cable shunt capacitance by means of resonance. The secondary inductance Ls of transformer 25 is selected such that it forms a parallel resonant circuit, at the respiration measurement frequency, with the cable shunt capacitance, Cc, and coupling capacitors, C1 and C2. Such a parallel L-C circuit presents a theoretically infinite shunt impedance at resonance. Therefore, impedance measuring circuit 46 is able to measure the resistive components of network 41 without interference from the cable shunt capacitance, Cc. However, this is only true if the resonance condition is maintained. If a different cable, having a different shunt capacitance, is used, the system will no longer be resonant at the operating frequency, and the shunting effects of the cable capacitance, or of the transformer inductance, will again begin to become apparent. Further, the cable's series resistors, if located between the transformer and the shunt capacitance, damp this resonance, reducing the efficacy of this method. In practice, this method is satisfactory only over a small range of cable capacitance, and therefore does not achieve the goal of making the respiration circuit substantially unaffected by the cable properties.

Coupling capacitors C1 and C2 are effectively in series with the impedance to be measured. The reactance of these capacitors must be kept fairly small if the patient impedance is to be easily measured through them. This can result in a capacitor value large enough to be objectionable from the standpoint of degradation of ECG performance, as has been described above. Circuit 28 in FIG. 4 illustrates an alternate form of the prior art, solving this problem by the use of what is commonly known as a "4-terminal" impedance measurement technique. Here, the current source 26 and the voltage measuring device 27 are coupled to the ECG cable through separate paths. The measurement current is coupled through capacitors labeled C1 and C2. These can present a fairly high impedance at the measurement frequency, since current source 26 will still force the desired current I through them. The voltage developed across network 42 is observed through coupling capacitors labeled C3 and C4. If voltage measurement device 27 has a very high input impedance at the respiration measurement frequency, these capacitors can be made very small. In practical circuits, all capacitors can be reduced to a few hundred picofarads or less, so that their impedance is extremely high at ECG band frequencies. Therefore, capacitors C3 and C4 provide excellent common and differential mode isolation for the ECG signals.

In some commercial instruments using the above coupling method, current source 26 is replaced by a voltage source. In this case, the coupling network, generally consisting of a series R-C network, is designed to have a rather high impedance at the measurement frequency. A voltage source with a high impedance in series will deliver an approximately constant current to a load, provided that the voltage drop developed in the load is much less than the source voltage. In this case, the coupling network provides this high impedance. The coupling network must contain small capacitors to provide a very high impedance to ECG band signals, and may optionally contain series resistance as well. The phase shift given to a sinusoidal drive voltage will be a function of the resistive and reactive components of the coupling network impedance.

A synchronous demodulator is often used for voltage measuring device 27. The use of a synchronous demodulator is advantageous, because it rejects interfering signals not harmonically related to the measurement frequency. The demodulator uses the driving voltage source as a reference. The phase of the reference must be selected taking into account the phase shift in the coupling network when loaded by the patient and cable. Optimal selection of the demodulator reference phase can minimize the variation in sensitivity due to changes in baseline resistance and cable capacitance, but not eliminate them. Therefore, while this method provides a simple means of coupling the respiration signal with minimal impact on the ECG circuits 44, it is still troubled by variation in sensitivity with changing cable capacitance and baseline resistance.

In some cases, other waveforms are more conveniently used than sinusoids. It is therefore also common practice for the current driven into the impedance under measurement to be approximately a square wave. Such a current may be sourced from a square wave voltage generator using a coupling network having a primarily resistive impedance at the measurement frequency. Alternatively, it may be derived from a triangle wave voltage generator, using a primarily capacitive coupling impedance, which essentially differentiates the triangular waveform. These methods are suitable for use with synchronous demodulation, and may be optimized by adjustment of the demodulator reference phase, just as in the case of a sinusoidal waveform. Nevertheless, these methods still show marked variation in sensitivity with changes in cable capacitance and patient resistance.

A superior method, embodied in the present invention, utilizes the 4-terminal measurement method with small coupling capacitors discussed above, and retains all the advantages of that method. However, it is distinct from the prior art, in that the measuring current waveform has a unique shape, such that the response is quite insensitive to cable shunt capacitance and patient baseline resistance over a very wide range. In the preferred embodiment, the uniquely shaped measuring current is provided by particular selection of the coupling components.

To illustrate the innovative technique of the present invention, embodied in the preferred embodiment illustrated in FIG. 6, first consider circuit 31 in FIG. 5. The object of the invention is to measure the resistive component alone of network 29. Network 29, circumscribed by a dotted line, consists of a number of series connected resistors and shunt capacitors, and may be considered a more generalized form of the cable and patient equivalent network 18 of FIG. 1C. Although three R-C sections are shown, it is understood that this is illustrative only, and an arbitrary number may be present.

Circuit 31 comprises a reservoir of charge 30 in the amount Q, a switch labeled S, and a voltage integrator 32. Reservoir 30 and switch S are in parallel with network 29 in one branch and voltage integrator 32 in another branch. The initial condition of the integrator 32 is zero, and switch Sis open. When switch S is closed, the charge Q is transferred as an impulse to network 29, which develops a transient voltage, eventually decaying to substantially zero. Integration is allowed to proceed from the instant of closing the switch until the transient voltage has decayed substantially to zero. At this point, the final value of the integrator output, Vi, divided by Q is equal to the sum of all series resistances in network 29, independent of the values of the capacitors in the network 29. Accordingly, circuit 31 can be used to accurately measure the resistance of a patient despite the existence of cable shunt capacitance.

The ability of circuit 31 to produce the resistance of the network 29 independent of the values of the capacitors of the network 29 can be demonstrated as follows: Injection of charge Q as an impulse is equivalent to injecting a current pulse with the form of a unit impulse, δ(t), times magnitude Q, or Q·δ(t). The unit impulse, δ(t), is a hypothetical pulse of zero width, infinite amplitude, and unity area. Network 29 presents a complex impedance labeled Z at its terminals. In the Laplace transform domain, the voltage V(s) developed across impedance Z(s) by current I(s) is simply V(s)=I(s)·Z (s). However, note that I(s)=Q·δ(s), and that the Laplace transform of δ(t), or δ(s), is unity. Therefore, the voltage developed across network 29 in response to the impulse is:

$$V(s) = Q \cdot Z(s) \tag{1}$$

This voltage represents the input to integrator 32. The Laplace transform of the integration operator is 1/s. Therefore, the output of integrator 32, Vi(s) is:

$$Vi(s) = \frac{1}{s} V(s) \tag{2}$$

or, substituting equation 1 for V(s):

$$Vi(s) = Q\left[\frac{1}{s} Z(s)\right] \tag{3}$$

Now consider the response of network 29 to a unit current step, u(t). The laplace transform of u(t) is 1/s, so the response of the network to the unit current step is Z(s)/s. Hence, the quantity in brackets in equation (3) will be recognized to be the unit current step response of network 29. Therefore, the response Vi(t) of integrator 32 in circuit 31 is the same as the voltage, V(t), that would be induced in network 29 by a current step of magnitude Q amperes.

A current step of amplitude I applied to network 29 induces a transient voltage V(t), exponentially approaching a steady state value of V=I·R, where R is the sum of all the series connected resistances within network 29. Since it has been demonstrated that integrator output Vi(t) in FIG. 5 is identical to V(t), the final value of the integrator output Vi is just Q·R, provided that integration is allowed to proceed until the transient behavior of network 29 has substantially died out.

Therefore, it is possible, to measure solely the resistive component of the impedance of network 29, without influence from the capacitive components, using the method disclosed above in conjunction with circuit 31. A continuous measurement may be performed by repeating the process of injection of charge and integration, with integrator 32 being reset to zero before each repetition. Of course, the period of each measurement cycle should be made long enough such that all transient behavior of network 29 substantially dies out during each cycle. In continuous measurement, the cumbersome process of resetting integrator 32 following each cycle can be eliminated by substituting a low pass filter for the integrator, as is done in the preferred embodiment below. When this low pass filter has a cutoff frequency well below the repetition rate of the charge injection, the filter's steady-state output will be proportional to that obtained at the end of each integration period.

The above method of continuous measurement is objectionable, because the continuous pulses, being all of the same polarity, induce a DC component across network 29, which could cause ECG interference and electrode polarization. Further, the desirable method of capacitive coupling cannot be used, due to this DC component. However, these objections can be overcome, as discussed with regard to the preferred embodiment below, by making the charge impulses alternate in polarity, and considering the absolute value of Vi. The resulting signal applied to the electrodes then has no net DC component, and may therefore be capacitively coupled. Further, if the impulse repetition frequency lies above the ECG bandpass, while still being low enough to allow for the decay of the transient behavior as discussed above, interference to ECG circuits will be avoided.

A means for generating the repetitive charge injection with alternating polarity may be realized as follows: A close approximation of charge injection as an impulse may be conveniently generated passing a voltage step through a small capacitor, used to couple the voltage step generator to network 29. If the amplitude of the voltage step is much larger than the voltage developed across network 29, the charge injected will be substantially independent of the impedance of network 29, and is given approximately by Q=Vs·C, where Vs is the amplitude of the step, and C the value of the capacitor. Repetitive measurement is possible by substituting a square wave for the voltage step. Alternating positive and negative charges will be injected on the rising and falling edges, respectively, of the square wave. The period of the square wave is chosen to be long enough such that the voltage developed across network 29 is able to decay substantially to zero during each half cycle. The resulting train of positive and negative transient voltages developed across network 29 is then rectified, or demodulated, to produce a train of transients of a single polarity. A low pass filter extracts the average value of this train of transients, performing a function equivalent to integrator 32. In the case of full-wave rectification, the average voltage, Vavg, is related to the integrator final voltage, Vi, discussed above, by:

$$Vavg = 2 \cdot f \cdot Vi \tag{4}$$

where f is the frequency of the square-wave generator.

FIG. 6 shows a preferred embodiment of the present invention, comprising circuit 36 operating on the principle described above and incorporating voltage generator 33, which produces a square wave of amplitude Vs, network 39, circumscribed by a dotted line, low pass filter 35, demodulator 34, a pair of capacitors labeled 2Ci, and a pair of capacitors labeled Cv. In keeping with the principle of a balanced, symmetrical circuit, the coupling, or charge injection, capacitance, Ci, has been divided into two equal portions, which effectively become series connected, and therefore each have double the value of Ci, namely 2Ci. The square-wave voltage generator 33, together with capacitance Ci, injects a train of charge impulses of alternating polarity into network 39. Network 39 represents the patient and cable impedance being measured. Demodulator 34 receives the differential voltage developed across network 39 by the injected charge, through coupling capacitors Cv. Demodulator 34 performs the function of demodulation, but may also contain a preamplifier, buffers, or a differential amplifier to receive the differential voltage signal. For purposes of discussion, demodulation is assumed to be performed by an absolute value function, designated |X|, equivalent to full-wave rectification. However, other forms of demodulation are possible, and indeed preferable, as is discussed below. The output of demodulator 34 is then filtered by low pass filter 35, which has a cutoff frequency much lower than the frequency of voltage generator 33, but sufficiently high to pass the respiratory modulation. The low pass filter 35 therefore extracts the average value of the train of voltage transients produced on the output of demodulator 34, but is still able to respond to respiratory modulation. The output of low pass filter 35 is proportional to the resistive component of the impedance of network 39, without influence from the capacitive components.

The process of taking the absolute value, designated above by |X|, is a specific method of the general process of demodulation of the voltage developed by the injected charge. Since the voltage developed across network 39 alternates in polarity, corresponding to the alternations in polarity of the injected charge, it has zero net DC value, and low pass filter 35 will not recover a signal unless some demodulation means is employed.

Various demodulation methods could be utilized by demodulator 34. The simplest method of demodulation is to allow only voltages of a single polarity to reach the low pass filter 35. This is analogous to a process of half-wave rectification, and may be performed with a device as simple as a diode, or more complex active rectifier circuits familiar to those skilled in the art. Half-wave rectification, however, discards half of the signal, since only the voltage corresponding to every other injection of charge is applied to the low pass filter 35. Therefore, the voltage output of the filter 35 is half of that predicted by equation 4. Equation 4 was developed assuming the demodulator to have an effect equivalent to the absolute value function, |X|. This is analogous to the process of full wave rectification. Various circuits capable of performing full wave rectification are well known. However, both of these simple rectification methods of demodulation suffer from the fact that they will respond to noise or extraneous signals as well as to the voltage developed across the network 39 by the charge injections.

In light of the above shortcoming, the preferred embodiment of the present invention uses synchronous demodulation for demodulator 34. In this case, demodulator 34 effectively multiplies the voltage received from the network 39 by the voltage of generator 33, and provides this product to the low pass filter 35. This may be accomplished by circuits capable of actual multiplication, such as an analog multiplier. However, the square wave generator output has only two states, which may be designated as −V and +V. Therefore, the demodulation can also be performed by a circuit having a gain that can be inverted in sign, corresponding to the state of the square wave generator. This may be accomplished by simple switching circuits. Since the respiration voltage generally exists as a differential and balanced signal, the voltage induced by the injection of charge is generally received by a differential amplifier or buffer, as part of demodulator 34. Synchronous demodulation can therefore be conveniently accomplished by passing the differential signal through an electronic DPDT switch, arranged to provide polarity reversal in response to the state of the square wave generator. This and other means of synchronous demodulation are well known to those familiar with the art. A synchronous demodulator operating with a square wave as the reference signal effectively rejects noise and other extraneous signals not harmonically related to the respiration measurement frequency. It is well known that such a demodulator only exhibits sensitivity to signals in narrow bands at the fundamental and odd harmonics of the measurement frequency, the width of these bands being determined by the low pass filter bandwidth. This is because the square wave reference signal, when subject to Fourier analysis, has only odd harmonics. Therefore, the synchronous demodulator of the preferred embodiment is superior to simple rectification techniques, in terms of noise rejection.

While the process of demodulation and filtering has been discussed in terms of analog circuits, those familiar with the art will recognize that some or all of these functions may be performed by digital means. An analog to digital converter may be introduced at any point in the signal processing path, with subsequent processing being performed digitally, including by means of software algorithms. Further, it is understood that certain types of analog to digital converters, such as dual-slope and delta-sigma types, are inherently capable of integration or low pass filtering, and may therefore be used to advantage to incorporate these functions. Furthermore, these and other converter types may permit the process of demodulation to be performed by the converter itself, such as by supplying the converter's reference voltage terminals from the square wave generator used to produce the charge injection.

The function of the low pass filter 35 is to reconstruct the respiratory modulation from the voltage waveform received from the demodulator 34. The demodulator output voltage is rich in components at the measurement frequency and harmonics thereof. The respiratory modulation occurs at much lower frequencies. Therefore, the low pass filter 35 is designed to strongly reject frequencies at the measurement frequency and above, while passing the much lower frequencies associated with the respiratory modulation. Low pass filter 35 therefore extracts the average value of the demodulator output voltage, corresponding to the respiratory signal, while still passing the respiratory modulations of this signal. Because these frequencies are widely separated, a very simple filter, such as a single pole R-C filter, may prove adequate for this purpose. However, this filter can also be used to shape the bandpass of the recovered respiratory signal, in which case a more complex filter may be required. Alternately, separate filter stages may be used. Any or all of these filters may be implemented as passive or active analog filters, or as digital filters, including software algorithms, when the implementation provides digitized data as discussed above.

It is helpful to minimize the amount of extraneous signal that can reach demodulator 34, even when the synchronous demodulator is used. Examples of such signals to be avoided are the patient's ECG signal and power-line frequency pick-up. Since these are comparatively low frequencies, they can be blocked by a high pass filter preceding demodulator 34. In the preferred embodiment, this is achieved by simply coupling demodulator 34 to the ECG electrodes through small-value capacitors, labeled Cv in FIG. 6, which together with the input resistance of demodulator 34 form a high pass filter. Further, high voltage surges may be present on the ECG leads during defibrillation of the patient. The respiration electronics should be protected from these surges. The small-value capacitors Ci and Cv used to couple the respiration circuits, both the generator 33 and demodulator 34, greatly facilitate blocking the harmful effect of defibrillator surges.

The arrangement of circuit 36 in FIG. 6 appears quite similar to the prior art 28 of FIG. 4. Note that measuring instrument 27 in prior art 28 of FIG. 4 may include a demodulator and filter, bearing resemblance to demodulator 34 and filter 35 of FIG. 6. However, in the prior art 28 of FIG. 4, the voltage generator 26 and the coupling impedances are chosen to impress a sinusoidal or roughly square-wave current on the impedance to be measured. In the case of circuit 36 of FIG. 6, the generator 33 and coupling elements are chosen to instead impress a brief transient spike of current, approximating injection of charge as an impulse.

These modifications to the prior art cause the subject invention to exhibit markedly different and superior characteristics when challenged by variation of cable shunt capacitance, cable series resistance, and patient baseline impedance.

The charge injected into the impedance to be measured is ideally in the form of an impulse of current. However, practical circuits can only approximate an impulse, and the pulse of current will have a finite width and some particular shape. The form of the current pulse is influenced by the risetime of the square wave generator, its output impedance, the network being measured, and the coupling capacitor value. In practice, it is desirable to limit the risetime of the generator. This reduces the instantaneous peak current that flows into the network, and further reduces the likelihood of the respiration circuit generating electromagnetic interference. This controlled risetime may be an inherent characteristic of the generator itself, or may be produced by active or passive low pass filter networks connected between the generator and the coupling capacitors. In some cases, it may become desirable to include a small amount of resistance in series with the coupling capacitors. For example, such resistance may facilitate protecting the generator circuits from the effects of an electrostatic discharge (ESD) applied to the patient connections of the device. Although the theory of operation has been explained assuming charge to be injected as an ideal impulse, these non-ideal conditions do not materially affect operation. However, best accuracy is obtained when the duration of the current pulse passed through the coupling capacitor is short relative to the half-period of the generator. This implies that the risetime of the generator, or filtered output thereof, be kept to a small fraction of its period. Further, if accuracy degradation is to be avoided, the value of resistance placed in series with the coupling capacitors cannot be excessive. In particular, best accuracy is obtained when the voltage drop across this resistance is small compared to the voltage impressed across the coupling capacitor.

It has been shown that the rise time of the generator need not be infinitely fast, and that a slower risetime may in fact be desirable. Further, the duty cycle of this generator need not be exactly 50%. An asymmetrical duty cycle may be used, provided that both portions of the pulse waveform are long enough in duration to meet the criteria outlined below. Therefore, although the generator may be commonly referred to as a square wave generator, it is recognized that the signal need not be exactly an ideal square wave. In recognition of the possibility of asymmetrical duty cycle and finite rise time, the generator could more generally be described as a substantially rectangular pulse generator.

While the preferred embodiment uses a voltage generator and coupling capacitors to inject charge, other means will be evident to those skilled in the art. For example, current sources arranged to be gated on for brief periods could be used for the injection of charge. The coupling capacitors and voltage generator inject a charge approximated by Q=Vs·C, as has been discussed. A gated current source of magnitude I injects charge given by Q=I·Δt, where Δt is the duration for which the current source is gated on. Note that the duration of Δt is subject to the same constraints as the risetime of the voltage generator discussed above. Suitable current sources can be made with transistors, FETs, or other means known to those familiar with the art. Therefore, while the preferred embodiment uses a particular means of injecting charge, it is recognized that other means can be used within the context of the present invention.

Figure 7:
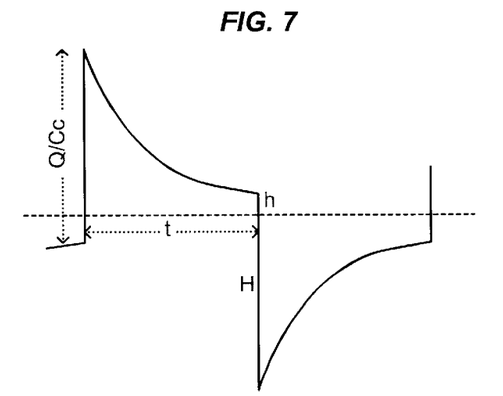
FIG. 7 is a plot of the general form of the voltage waveform produced by the circuit of FIG. 6.

In the foregoing theory of operation, it has been assumed that the transient voltage developed in the network fully decays before the next impulse of charge is applied. Complete decay of course requires infinite time, so in practice a compromise is made in which some small residual voltage still exists when the next charge impulse is applied. FIG. 7 shows the transient voltage waveform that exists across the impedance being measured when circuit 36 of FIG. 6 is operated under these conditions. The small residual voltage, h, exists due to the finite time, t, allowed for decay. Analysis of circuit 36, assuming synchronous demodulation in demodulator 34, shows the steady-state value of the average voltage, Vf, extracted by the lowpass filter 35 is:

$$Vf = R\frac{Q}{t}\left[\frac{1 - e^{-t/CcR}}{1 + e^{-t/CcR}}\right] \quad (5)$$

Where R is the total equivalent resistance of the cable and patient, Rd+Rp+Rd in FIG. 6, and t is the half period of the square wave. When t is made very large, the quantity in square brackets approaches unity, and equation 5 simplifies to Vf=RQ/t. In this case Vf becomes linearly dependent on R without influence by Cc, as is desired. For finite values of t, an error in sensitivity is produced. If t is fixed by design, this error varies as Cc and R change. By selecting t to be somewhat greater than the worst-case (maximum) anticipated product of Cc times R, the error can be contained to as small a value as desired. For example, consider respiration circuit 36 where t is made 3 times greater than the worst-case (maximum) product of Cc and R, for the range of cables and patients resistances to be considered. Evaluation of the quantity in brackets shows that it varies from unity to approximately 0.9 as a function of Cc and R. Therefore, the sensitivity of circuit 36 under these conditions will not drop by more than 10% as Cc and R are varied within their worst-case range.

In practice, the selection of t, and hence the operating frequency, is still a compromise, although a far more favorable compromise than in the prior art. In both cases, the measurement frequency should be kept well above the ECG bandpass to avoid ECG interference. Further, in both cases this requirement is balanced by the fact that lower operating frequencies provide greater immunity to changes in sensitivity as a function of Cc and R. However, for a given operating frequency, the present invention will offer superior characteristics to the prior art. Consider the case of the prior art utilizing a 50 kHz sinusoidal measurement current analyzed in FIG. 2. The maximum value of Cc shown in FIG. 2B is 740 pF, and the maximum value of R is 4500 ohms (Rp=2500, plus Rd=2×1000). Under these maximal conditions, the sensitivity of the prior art circuit 19 (FIG. 2A) dropped over 3:1 compared with the case where Cc and Rp were minimum, as is illustrated in FIG. 2C. Now consider these same operating parameters applied to the present invention, as shown by circuit 36. At a frequency of 50 kHz, the square wave period is 20 μs, so t is 10 μs. The product of the maximum Cc and maximum R is 3.33 μs. This value is one-third of t. Based upon the example above, it is known that the change in sensitivity for the present invention will not exceed 10%, which is far less than the 67% exhibited by the prior art under the same conditions. Further, if t were extended to 15 μs, making the frequency 33.3 kHz, the sensitivity change under the same maximal conditions drops to just 2% for the present invention, while the prior art exhibits a variation of some 45%. Therefore, as the frequency is reduced, the performance of the present invention, circuit 36, improves more rapidly than that of the prior art circuit 19.

It is understood that while this invention has been described in specific terms of monitoring the respiration of a patient, the scope of application is not limited by this description. The concept of a patient includes not only humans, but also any living organism in which measurement of tissue impedance is desirable. Further, although the modulation of tissue impedance by respiration has been discussed, it is known to those familiar with the art that the impedance of tissue varies with other factors, such as blood content. It is understood that this invention may be applied to any measurement of tissue impedance. Finally, it is understood that this invention may be applied to the general measurement of resistance in the presence of shunt capacitance, even when the resistance-capacitance network involved does not contain the tissue of an organism.

I claim:

1. An apparatus for measuring the resistive component of the impedance of a network having shunt capacitance, comprising:
   (a) A generator device for injecting a known quantity of charge to the network, said network comprising one or more cables connected to electrodes in contact with the tissue of a patient, said charge inducing a voltage across the network; and
   (b) An integrator connected to said network for integrating said voltage, the result of said integration being indicative of the resistive component of the impedance of the network.

2. The apparatus of claim 1 wherein the generator device is coupled through a coupling capacitor connected to the network.

3. An apparatus for measuring the resistive component of the impedance of a network having shunt capacitance, comprising:
   (a) A generator device for repeatedly injecting a known quantity of charge to the network, said network comprising one or more cables connected to electrodes in contact with the tissue of a patient, said charge inducing a voltage across the network;
   (b) A demodulator connected to said network for demodulating the voltage;.and
   (c) A low pass filter connected to the demodulator, the output of said low pass filter being indicative of the resistive component of the impedance of the network.

4. The apparatus of claim 3 wherein the generator is coupled through a coupling capacitor connected to the network.

5. The apparatus of claim 3 wherein alternate injections of charge have opposite polarity.

6. A method for measuring the resistive component of the impedance of a network having shunt capacitance, comprising the steps of:
   (a) Applying a known quantity of charge to the network, said charge inducing a voltage across the network; and
   (b) Integrating said voltage over a predetermined time period, the result of said integration being indicative of the resistive component of the impedance of the network.

7. The method of claim 6, further comprising the step of evaluating the degree of acceptable measurement error of the resistive component of the impedance of the network and choosing the time period accordingly, a longer time period results in a more accurate resistive component measurement and a shorter time period results in a less accurate resistive component measurement.

8. The method of claim 6 wherein the charge is injected over a brief period approximating an impulse.

9. The method of claim 6 wherein steps (a)–(c) are repeated at least once so as to allow changes in the impedance of the network to be monitored.

10. The method of claim 9, wherein the applied charge alternates in polarity after each repetition of steps (a)–(c).

11. The method of claim 1, wherein a coupling capacitor is connected to the network for application of the charge, said charge being applied by passing a voltage step through the coupling capacitor.

12. The method of claim 10 wherein a coupling capacitor for application of the charge is connected to the network, said charge alternating in polarity and applied by passing a substantially rectangular repetitive pulse waveform through the coupling capacitor.

13. The method of claim 9, wherein the network comprises one or more cables connected to electrodes in contact with tissue of a patient.

14. The method of claim 13, wherein an impedance of said tissue varies with each respiratory cycle of the patient.

15. The method of claim 13, wherein an impedance of said tissue varies with the blood content of the tissue.

16. A method for measuring the resistive component of the impedance of a network having shunt capacitance, comprising the steps of:
   (a) Repeatedly applying a known quantity of charge to the network, said charge inducing a voltage across the network;
   (b) Passing said voltage through a low pass filter, the output of the low pass filter being indicative of the resistive component of the impedance of the network.

17. The method of claim 16 wherein the charge alternates in polarity and further comprising the step of passing the voltage through a demodulator connected to the network prior to passing it through the low pass filter.

18. The method of claim 16 wherein the charge alternates in polarity with each application of charge to the network, said charge alternating in polarity being produced by passing a substantially rectangular repetitive pulse waveform through a coupling capacitor.

19. The method of claims 17 or 18, wherein the demodulator is a half-wave rectifier.

20. The method of claims 17 or 18, wherein the demodulator has the function of an absolute value operation.

21. The method of claims 17 or 18, wherein the demodulator is a synchronous demodulator.

22. An apparatus for measuring the resistive component of the impedance of a network having shunt capacitance, comprising:
   (a) A means for applying a known quantity of charge to the network, said charge inducing a voltage across the network; and
   (b) A means for integrating said voltage over a predetermined time period, the result of said integration being indicative of the resistive component of the impedance of the network.

23. The apparatus as claimed in claim 22 wherein the time period is chosen to attain the desired degree of accuracy of the integration result, a longer time period results in a more accurate integration result and a shorter time period results in a less accurate integration result.

24. The apparatus as claimed in claim 22 wherein the means for applying the charge injects the charge over a brief period approximating an impulse.

25. The apparatus as claimed in claim 22 wherein the means for applying the charge injects repetitively.

26. The apparatus as claimed in claim 25 wherein alternate injections of charge have opposite polarity.

27. The apparatus of claim 22, wherein said means for applying charge comprises a voltage step generator coupled through a capacitor.

28. The apparatus of claim 22, wherein the means for applying the charge injects repetitively and wherein alternate injections of charge have opposite polarity, said means for applying charge comprising a substantially rectangular repetitive pulse generator coupled through a capacitor.

29. The apparatus of claim 22, wherein the network comprises one or more cables connected to electrodes in contact with the tissue of a patient.

30. The apparatus of claim 29, wherein an impedance of said tissue varies with each respiratory cycle of the patient.

31. The apparatus of claim 29, wherein the impedance of said tissue varies with the blood content of said tissue.

32. An apparatus for measuring the resistive component of the impedance of a network having shunt capacitance, comprising:
   (a) A means for applying a known quantity of charge to the network, said charge inducing a voltage across the network; and
   (b) A means for low pass filtering said voltage, the result of said low pass filtering being indicative of the resistive component of the impedance of the network.

33. The apparatus of claim 32, wherein the means for applying the charge injects repetitively.

34. The apparatus of claim 33 wherein the injected charge alternates in polarity and wherein the apparatus further comprises a means for demodulating the voltage measured across the network.

35. The apparatus of claim 34, wherein the means for demodulating comprises a half wave rectifier.

36. The apparatus of claim 34, wherein the means for demodulating takes the absolute value of the voltage passed through it.

37. The apparatus of claim 34, wherein the means for applying charge comprises a substantially rectangular repetitive pulse generator coupled through a capacitor.

38. The apparatus of claim 37 wherein the means for demodulating comprises a synchronous demodulator referenced to said substantially rectangular repetitive pulse.

39. The apparatus of claim 37 wherein the means for demodulating comprises a half wave rectifier.

40. The apparatus of claim 37 wherein the means for demodulating takes the absolute value of the voltage passed through it.

41. The apparatus of claim 32 wherein the network comprises one or more cables connected to electrodes in contact with the tissue of a patient.

* * * * *